(12) United States Patent
Wu et al.

(10) Patent No.: US 9,709,538 B2
(45) Date of Patent: Jul. 18, 2017

(54) DEVICES TO DETECT A SUBSTANCE AND METHODS OF PRODUCING SUCH A DEVICE

(75) Inventors: Wei Wu, Palo Alto, CA (US); Zhiyong Li, Palo Alto, CA (US); Ansoon Kim, Palo Alto, CA (US); Min Hu, Palo Alto, CA (US); Michael Josef Stuke, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 482 days.

(21) Appl. No.: 14/239,330

(22) PCT Filed: Sep. 30, 2011

(86) PCT No.: PCT/US2011/054283
§ 371 (c)(1),
(2), (4) Date: Feb. 18, 2014

(87) PCT Pub. No.: WO2013/048446
PCT Pub. Date: Apr. 4, 2013

(65) Prior Publication Data
US 2014/0199778 A1    Jul. 17, 2014

(51) Int. Cl.
*G01N 31/22* (2006.01)
*G01N 21/64* (2006.01)
(Continued)

(52) U.S. Cl.
CPC ............ *G01N 31/22* (2013.01); *B01L 3/5085* (2013.01); *B01L 3/50853* (2013.01);
(Continued)

(58) Field of Classification Search
CPC ....................................................... G01N 31/22
(Continued)

(56) References Cited

U.S. PATENT DOCUMENTS 7,504,071 B2   3/2009  Blatter et al.
7,605,916 B2  10/2009  Zhang et al.
(Continued)

FOREIGN PATENT DOCUMENTS

| CN | 101629899 | 1/2010 |
| EP | 1536038 | 6/2005 |

(Continued)

OTHER PUBLICATIONS

International Search Report and Written Opinion, Korean IPO, Oct. 30, 2012. Hewlett-Packard Development Company, L.P., PCT Application No. PCT/US11/054283.
(Continued)

*Primary Examiner* — Christine T Mui
*Assistant Examiner* — Emily Berkeley
(74) *Attorney, Agent, or Firm* — Hanley Flight & Zimmerman, LLC

(57) ABSTRACT

Devices to detect a substance and methods of producing such a device are disclosed. An example device to detect a substance includes a housing defining an externally accessible chamber and a seal to enclose at least a portion of the chamber. The example device also includes a substrate includes nanoparticles positioned within the chamber. The nanoparticles to react to the substance when exposed thereto. The example device also includes a non-analytic solution within the chamber to protect the nanoparticles from premature exposure.

20 Claims, 10 Drawing Sheets

(51) Int. Cl.
*G01N 21/65* (2006.01)
*B01L 3/00* (2006.01)
*B82Y 15/00* (2011.01)

(52) U.S. Cl.
CPC ......... *G01N 21/648* (2013.01); *G01N 21/658* (2013.01); *B01L 2200/141* (2013.01); *B01L 2300/069* (2013.01); *B01L 2300/0636* (2013.01); *B01L 2300/0819* (2013.01); *B82Y 15/00* (2013.01); *G01N 2201/023* (2013.01); *G01N 2201/0227* (2013.01); *Y10T 436/25* (2015.01)

(58) Field of Classification Search
USPC .......................................................... 436/174
See application file for complete search history.

(56) References Cited

U.S. PATENT DOCUMENTS

| | | | |
|---|---|---|---|
| 2002/0153251 A1* | 10/2002 | Sassi | G01N 27/44743 204/455 |
| 2003/0157732 A1 | 8/2003 | Baker et al. | |
| 2004/0239044 A1 | 12/2004 | Blatter et al. | |
| 2007/0254377 A1 | 11/2007 | Li et al. | |
| 2010/0120132 A1 | 5/2010 | Koo | |
| 2010/0284001 A1 | 11/2010 | Moskovits et al. | |
| 2012/0113420 A1* | 5/2012 | Kuo | G01N 21/658 356/301 |

FOREIGN PATENT DOCUMENTS

| | | | |
|---|---|---|---|
| JP | H04-225145 | 8/1992 | |
| JP | H04-232444 | 8/1992 | |
| JP | 2001-249073 | 9/2001 | |
| JP | 2007-110962 | 5/2007 | |
| JP | 2010-271217 | 12/2010 | |
| WO | WO-2011/014176 | 2/2011 | |
| WO | WO-2011016888 | 2/2011 | |
| WO | WO-2011034533 | 3/2011 | |
| WO | WO 2011034533 A1 * | 3/2011 | ......... G01N 21/658 |
| WO | WO-2011037533 | 3/2011 | |
| WO | WO-2011047199 | 4/2011 | |
| WO | WO-2011063313 A1 | 5/2011 | |

OTHER PUBLICATIONS (Abstract) Self-assembled metal colloid monolayers.

* cited by examiner

DEVICES TO DETECT A SUBSTANCE AND METHODS OF PRODUCING SUCH A DEVICE

STATEMENT REGARDING FEDERALLY SPONSORED RESEARCH OR DEVELOPMENT

This invention has been made with government support under Agreement No.: HR0011-09-3-0002 awarded by Defense Advanced Research Projects Agency. The government has certain rights in the invention.

BACKGROUND

Surface Enhanced Raman spectroscopy (SERS) may be used in various industries to detect the presence of an analyte. For example, SERS may be used in the security industry to detect for explosives (e.g., detecting baggage at airports for explosives and/or other hazardous materials). Alternatively, SERS may be used in the food industry to detect toxins or contaminates in water and/or milk.

Figure 1:
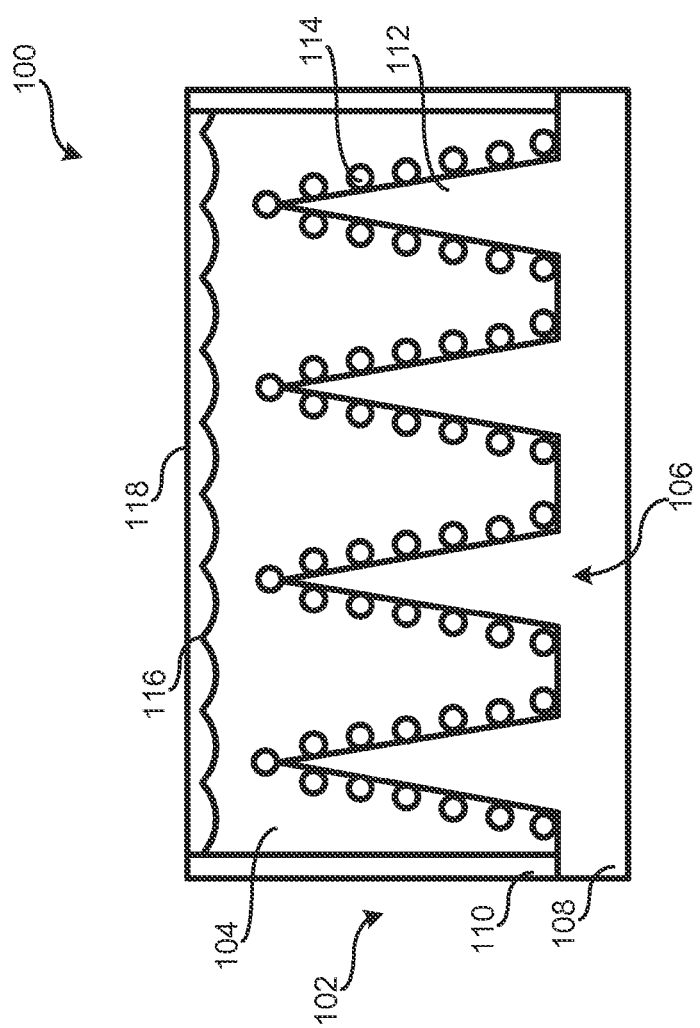
FIG. 1 depicts an example testing device constructed in accordance with the teachings of this disclosure.

Certain examples are shown in the above-identified figures and described in detail below. The figures are not necessarily to scale and certain features and certain views of the figures may be shown exaggerated in scale or in schematic for clarity and/or conciseness.

DETAILED DESCRIPTION

Many applications have a need for a reliable device that can be employed to detect the presence of a substance of interest. For example, such testing or detecting devices are useful to detect the presence of explosives, toxins or hazardous substances at airports, manufacturing facilities, food processing facilities, drug preparation plants, etc. The substrates of some known testing and/or detecting devices are not sufficiently protected against premature exposure to the environment and/or a substance (e.g., an analyte) that the substrate is intended to detect. Prematurely exposing the substrate to the environment and/or the substance (e.g., an analyte) may cause the substrate to oxidize and/or to not be as effective in detecting the substance once intentionally exposed thereto.

Example testing and/or detecting devices for the analysis of various substances are disclosed herein. In some such examples, the testing device is for use with surface Enhanced Raman spectroscopy, Enhanced Fluorescence spectroscopy or Enhanced Luminescence spectroscopy, which may be used to detect the presence of the substance of interest in or on the testing or detecting device. In contrast to some known devices, testing devices disclosed herein include non-analytic liquids or solutions that protect a substrate of the testing device from exposure to the environment and/or reduce or even prevent oxidation of the substrate and/or associated surface structures prior to use. More specifically, the non-analytic liquids or solutions reduce or even prevent the unintentional exposure of nanoparticles, metallic nanoparticles, nanostructures, SERS strip, etc., of the substrate to a substance such as an analyte that the nanoparticles, metallic nanoparticles or microparticles, nanostructures, SERS strip, etc., are intended to detect.

In some examples disclosed herein, the testing device includes a housing defining an externally accessible chamber or cavity. The housing in such examples includes a plurality of layers coupled together. The housing and/or one or more layers thereof may be made of glass, plastic, paper, Polydimethylsiloxane, rubber and/or a membrane. A substrate on which nanostructures and/or nanoparticles are disposed is positioned within the chamber. The nanostructures may be a plurality of conical structures, a plurality of pillar structures, etc., and/or may be at least partially transparent. The nanoparticles may be gold, silver, etc. The nanostructures and/or nanoparticles react to, secure or otherwise indicate exposure to a substance of interest (e.g., an analyte) when, for example, subjected to one or more examination techniques and/or analysis such as surface Enhanced Raman spectroscopy, Enhanced Fluorescence spectroscopy and/or Enhanced Luminescence spectroscopy. To prepare the testing device for such analysis, the nanostructures and/or nanoparticles are exposed to the environment which may contain the substance of interest (e.g., an analyte).

To protect the nanostructures and/or nanoparticles from premature (e.g., unintentional) exposure to the environment and/or the substance (e.g., an analyte present in the environment to be tested or another environment), in some examples, a non-analytic solution fills at least a portion of the chamber. The non-analytic solution may be water, distilled water, alcohol, ethanol, a hydrocarbon solution, a pure liquid, etc. The substrate and associated nanostructures and/or nanoparticles may be at least partially submerged and/or in the non-analytic solution.

To enclose the substrate and the non-analytic solution within the chamber, example testing and/or detecting devices disclosed herein include a seal removably coupled to the housing to enclose at least a portion of the chamber. The seal may be a hermetic seal made of plastic, plastic sheeting, foil, foil sheeting, a membrane, wax and/or Polydimethylsiloxane. In some examples, the seal is at least partially transparent to enable viewing and/or analysis of the substrate, nanostructures and/or nanoparticles prior to exposure to the environment and/or substance (e.g., an analyte).

In some examples, prior to exposing the substrate, nanostructures and/or nanoparticles, the seal and the non-analytic solution are at least partially removed from the chamber. In some examples, an absorbent is positioned adjacent the chamber and separated from the non-analytic solution by the seal prior to its removal. In such examples, when the seal is removed, the absorbent absorbs at least a portion of the non-analytic solution (e.g., through contact therewith). The absorbent may be a porous material, a hydrogel, etc. The chamber of some example devices disclosed herein includes a small amount of non-analytic solution (e.g., a few microliters). In other examples, after at least partially removing the seal, a person may use filter paper, paper, cloth, etc., to remove the non-analytic solution from the chamber. After the non-analytic solution has been absorbed and/or removed, the substrate, nanostructures and/or nanoparticles may be exposed to the environment, chemical, substance, gas, analyte, etc., to be tested.

In some examples disclosed herein, the testing device includes a housing defining one or more grooves into which removable testing strips or elongated bodies are positioned. The testing strips of some example devices include a substrate that extends into the groove and a portion that sealing engages against the housing. The substrate of such examples includes nanostructures and/or nanoparticles to detect a substance of interest (e.g., an analyte), as discussed above. The housing of such examples may be made of glass, plastic, paper, Polydimethylsiloxane, rubber and/or a membrane. The testing strips may be made of metal, plastic, etc.

To protect the nanostructures and/or nanoparticles from premature (e.g., unintentional) exposure to an environment, substance, analyte, etc., in disclosed examples, a non-analytic solution fills at least a portion of the grooves and at least partially submerges the substrate. To expose the substrate of the testing strips to an environment, chemical, substance, gas, analyte, etc., to be tested, one or more of the testing strips is removed from the housing. Removing the testing strip exposes the substrate. In some examples, an absorbent may be positioned adjacent the groove and separated from the non-analytic solution by the testing strip prior to its removal. In such examples, when the respective testing strip is removed from the housing, the absorbent comes in contact with the non-analytic solution and absorbs at least a portion thereof, thereby rendering the device operative for detection (e.g., analyte detection).

In some examples, after the substrate, nanostructure and/or nanoparticles have been exposed to the environment and/or substance (e.g., chemical, gas, analyte, etc.), whose presence is to be detected and/or tested, the testing device or strip is placed in or adjacent to an example reading device. The reading device may include a light source that illuminates the substrate, nanostructure and/or nanoparticles. In some examples, the light scattered by the substrate, nanostructure and/or nanoparticles (e.g., Raman scattering in Surface Enhanced Raman spectroscopy, fluorescence in Enhanced Fluorescence spectroscopy or luminescence in Enhanced Luminescence spectroscopy) is monitored using a spectrometer, photodetector, etc., having appropriate guiding and/or filtering components. In some examples, the results obtained by the reading device are displayed on a monitor and/or are indicative of detection or no detection of the substance being tested and/or looked for.

FIG. 1 depicts an example testing and/or detection device 100 constructed in accordance with the teachings of this disclosure. The testing device 100 includes a housing 102 defining a chamber 104 in which a substrate 106 is positioned. In the illustrated example, the housing 102 includes a first layer 108 coupled to a second layer 110. However, in other examples, the housing 102 may include any other number of layers (e.g., 1, 3, etc.). The housing 102 may be made of any suitable material such as glass, plastic, paper, Polydimethylsiloxane, a transparent material, rubber and/or a membrane, for example.

The substrate 106 of the illustrated example includes conical nanostructures 112 on which nanoparticles (e.g., metallic nanoparticles) 114 are positioned. The nanoparticles 114 may include gold and/or silver and/or any other element or chemical that may react with, respond to, collect, etc., a substance of interest such as an analyte. The nanostructures 112 and/or the nanoparticles 114 of the illustrated example facilitate detection of an analyte to which they have been exposed. For example, the substrate 106 may be illuminated and the resulting backscatter read using surface Enhanced Raman spectroscopy, Enhanced Fluorescence spectroscopy and/or Enhanced Luminescence spectroscopy to determine if spectral components indicative of the presence of the analyte of interest are generated.

To protect the nanostructures 112 and/or the nanoparticles 114 from premature and/or unintentional exposure to the environment and/or substances to which they may respond (e.g., an analyte), the chamber 104 of the illustrated example is at least partially filled with a non-analytic liquid and/or solution 116. Premature exposure may cause the nanostructures 112 and/or nanoparticles 114 to react or otherwise respond to a substance (e.g., an analyte) that is currently present in an environment not to be tested, but not actually present in the test environment of interest, thereby resulting in a false positive. The non-analytic solution 116 prevents such false positives. The solution 116 may be a solution and/or pure liquid. For example, the non-analytic solution may be implemented by water, distilled water, alcohol, ethanol and/or a hydrocarbon solution.

To enclose the chamber 104 of the illustrated example, a seal 118 is removably coupled to the housing 102. The seal 118 of the illustrated examples is a hermetic seal and may be made of plastic, a transparent material, plastic sheeting, foil material, foil sheeting, a membrane, wax and/or Polydimethylsiloxane. In some examples, the seal 118 is transparent to enable photons and/or light of a reading device to illuminate the chamber 104 and/or the substrate 106 to determine the presence or absence of the substance being tested for in the test environment.

Figure 2:
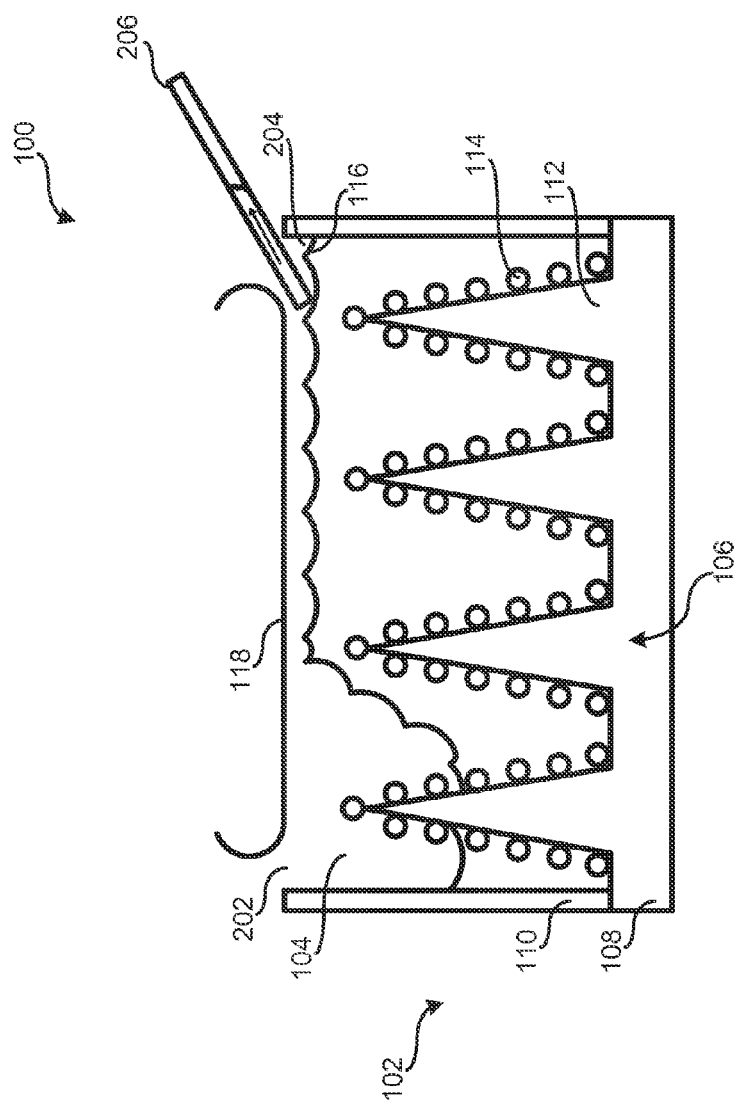
FIG. 2 depicts the example testing device of FIG. 1 with a seal partially removed and a non-analytic solution being removed from a chamber.

FIG. 2 depicts the example testing and/or detecting device 100 of FIG. 1 after the seal 118 has been partially removed to define an inlet 202 and an outlet 204. To enable the nanostructures 112 and/or nanoparticles 114 to be exposed to a test environment and/or possibility to a substance of interest such as an analyte, the non-analytic solution 116 of the illustrated example is removed by inserting a piece of paper or other object 206 having absorbent characteristics through the outlet 204 and into the non-analytic solution 116. As the non-analytic solution 116 is being absorbed by the paper 206, air and/or other gas within a test environment (e.g., a room) in which the testing device 100 is positioned flows through the inlet 202 and into the chamber 104 where it is exposed to the nanostructures 112 and/or nanoparticles 114. The air, other gas within the test environment and/or other gas may or may not include the analyte that the nanostructures 112 and/or the nanoparticles 114 are intended to detect.

Figure 3:
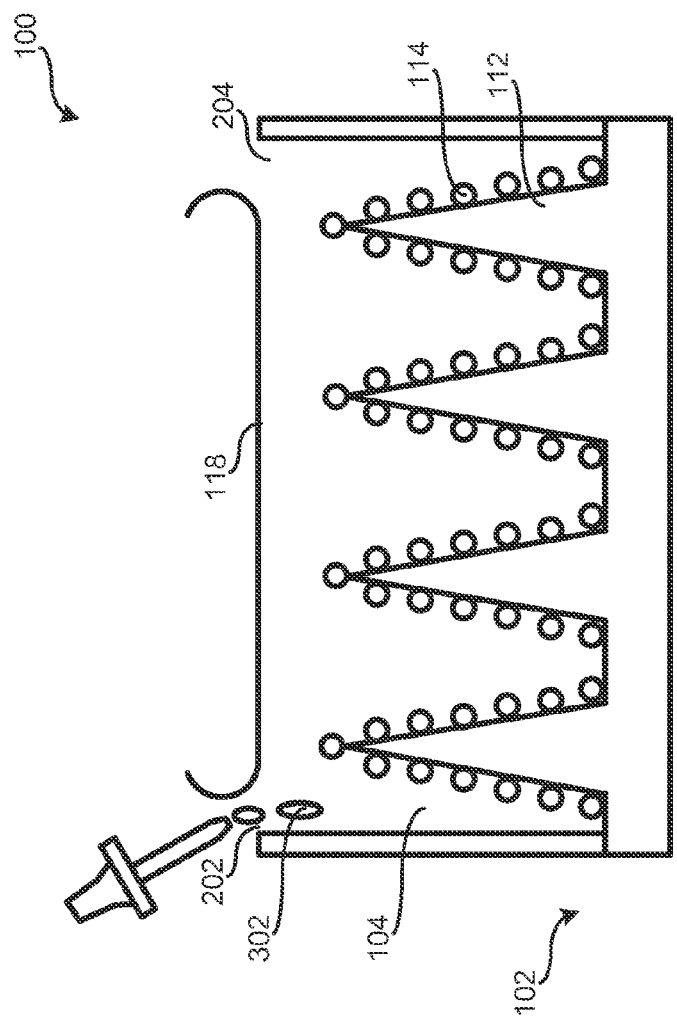
FIG. 3 depicts the example testing device of FIG. 1 with the non-analytic solution removed from the chamber and an analytic solution being added to the chamber.

FIG. 3 depicts the example testing and/or detecting device 100 with the seal 118 partially removed from the housing 102, the non-analytic solution 116 removed from the chamber 104 and a solution or chemical 302 to be analyzed being added to the chamber 104. The solution or chemical 302 may include the analyte that the nanostructures 112 and/or the nanoparticles 114 are intended to detect. In some example, after the nanostructures 112 and/or the nanoparticles 114 have been exposed to the solution or chemical, the chamber 104 is recovered by the seal 118 and/or another seal to ensure that the nanostructures 112 and/or nanoparticles 114 are not contaminated with exposure to a non-testing environment after the test has occurred.

Figure 4:
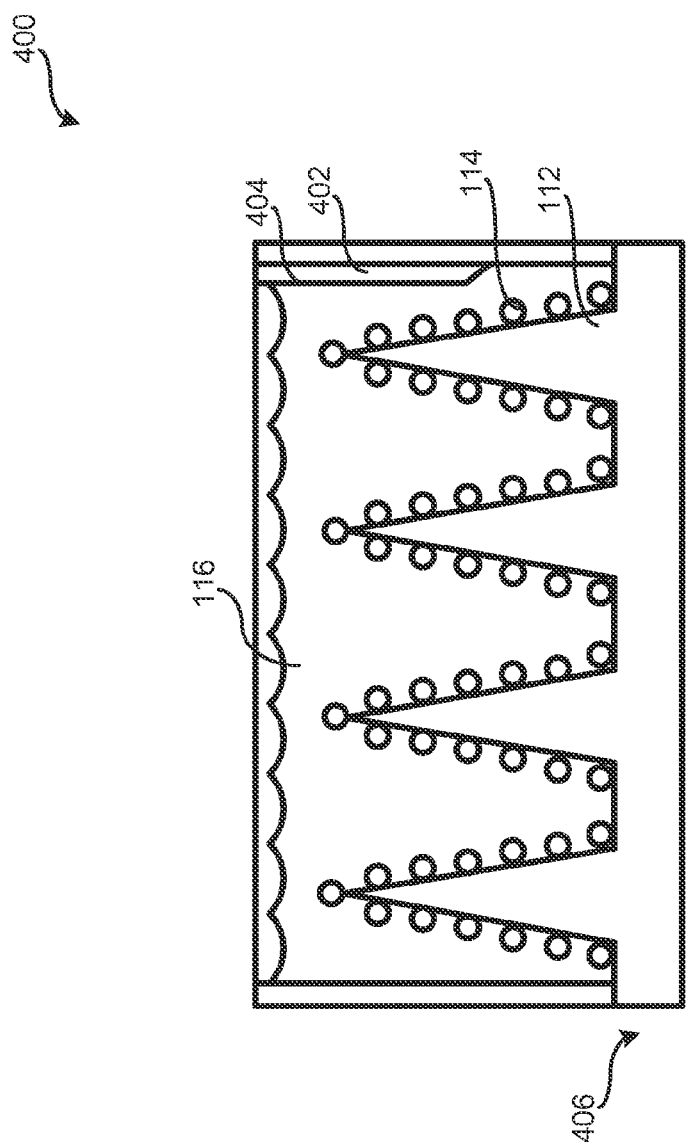
FIG. 4 depicts another example testing device constructed in accordance with the teachings of this disclosure and including an absorbent.

FIG. 4 depicts another example testing and/or detecting device 400. The example testing device 400 of FIG. 4 includes a housing 406 and an absorbent 402 that is separated from the non-analytic solution 116 by a seal 404. In practice, when the seal 404 is removed from the housing 406 of the testing device 400, the absorbent 402 is exposed to the non-analytic solution 116. As a result, the absorbent 402 absorbs at least a portion of the non-analytic solution. The absorbent 402 may be implemented by any desired absorbent material such as, for example, a porous material or a hydrogel.

Figure 5:
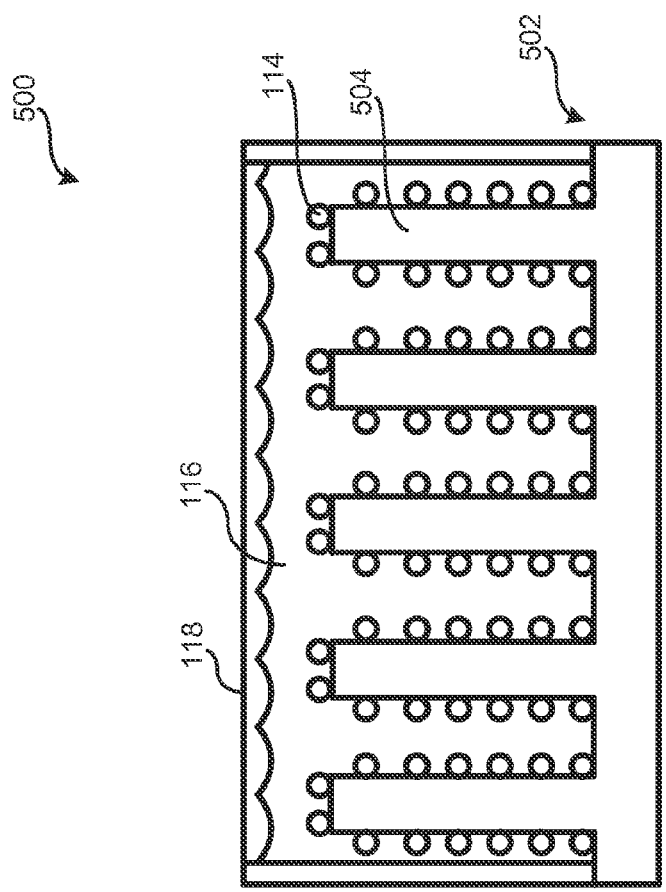
FIG. 5 depicts another example testing device constructed in accordance with the teachings of this disclosure.

FIG. 5 depicts another example testing and/or detecting device 500 constructed in accordance with the teachings of this disclosure. The example testing device 500 of FIG. 5 includes a housing 502, a seal 118, the non-analytic solution 116 and pillar nanostructures 504.

Figure 6:
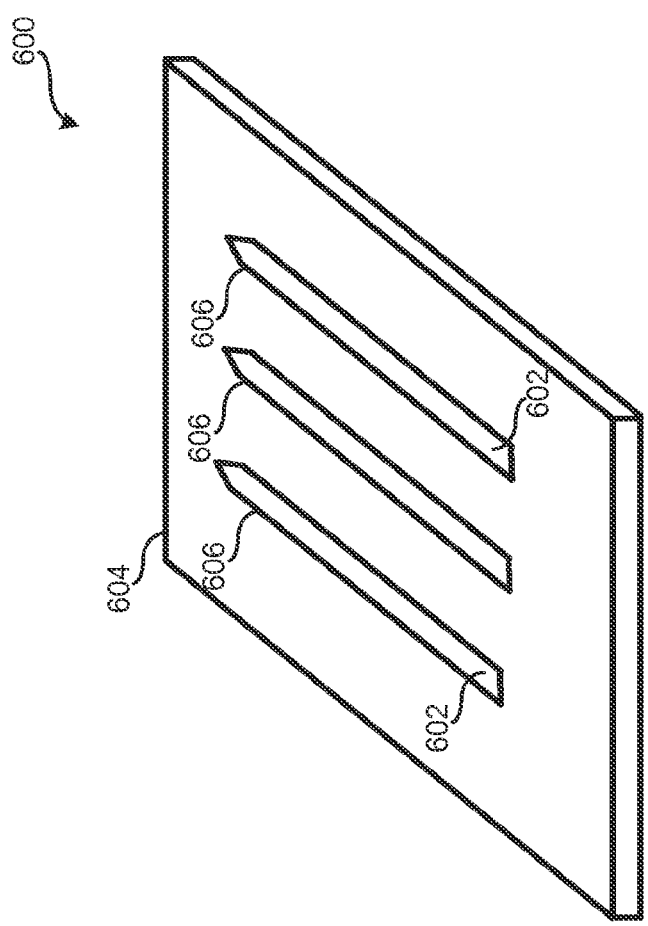
FIG. 6 depicts another example testing device constructed in accordance with the teachings of this disclosure.

FIG. 6 depicts another example testing and/or detecting device 600. The example testing device 600 of FIG. 6 includes a plurality of removable testing strips 602. The example testing strips 602 may be implemented as needles, pins or elongated bodies. The housing 604 of the example testing and/or detecting device 600 defines a plurality of grooves, chambers or cavities 606 in which the respective testing strips 602 are positioned prior to use. The testing strips 602 sealingly engage the housing 604 and enclose at least a portion of the respective grooves 606. In other examples, the testing device 600 is a piece of material having a flat surface to which the testing strips 602 are removably attached (e.g., secured with a releasable glue having low bond strength). In this example, the housing 604 does not have grooves 606.

Figure 7:
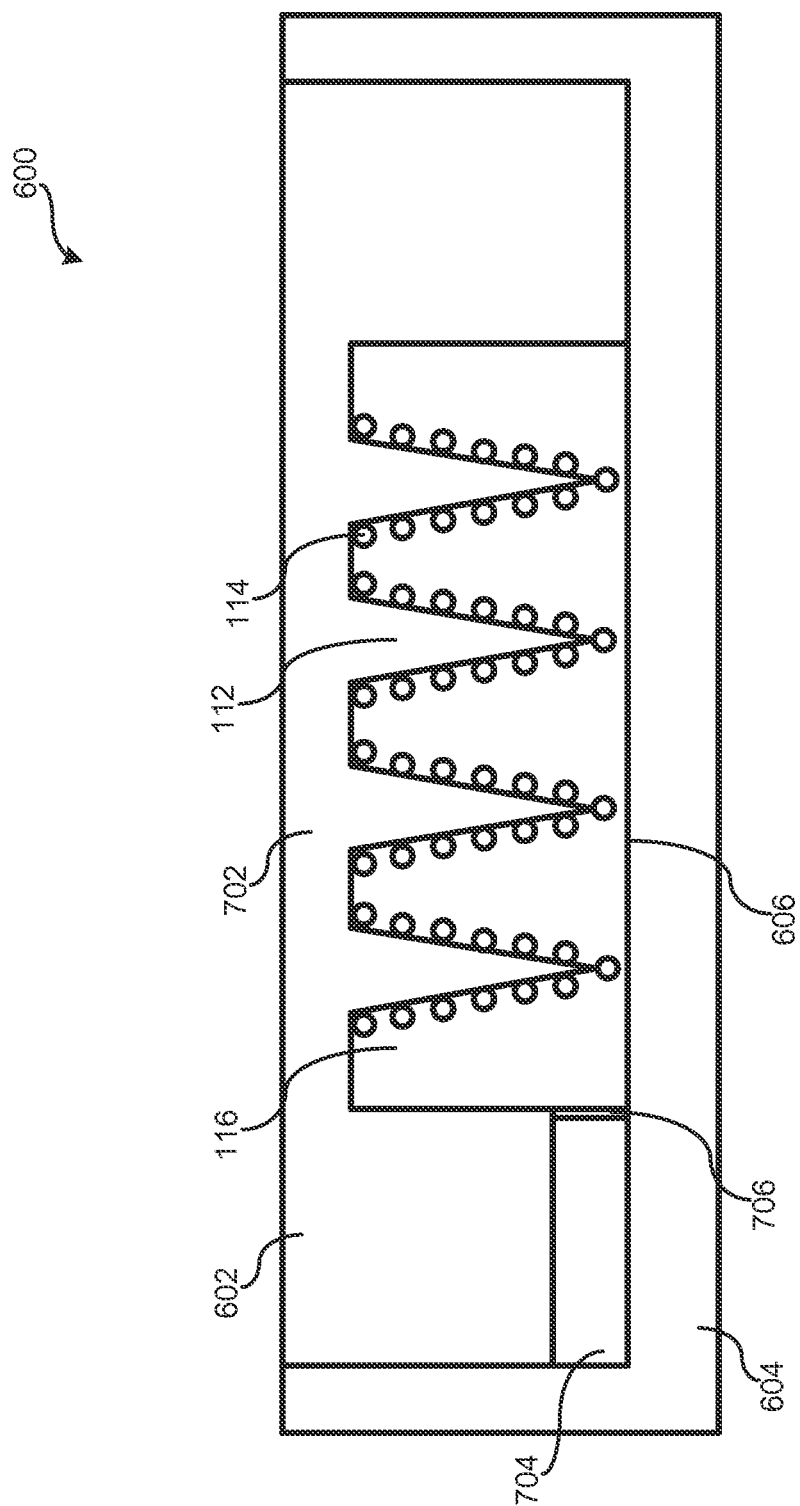
FIG. 7 is a cross-sectional view of the example testing device of FIG. 6.

FIG. 7 is a cross-sectional view of the example testing and/or detecting device 600 of FIG. 6. As shown in FIG. 7, the testing strip 602 includes a substrate 702 that is positioned within the groove 606. The substrate 702 of this example includes the nanostructures 112 and the nanoparticles 114.

To protect the nanostructures 112 and/or the nanoparticles 114 from premature and/or unintentional exposure to the environment to be tested and/or substance to be detected, the groove 606 of the illustrated example is filled with the non-analytic solution 116. In the illustrated example, the testing strip 602 sealing engages against the housing 604 to enclose the nanostructures 112, the nanoparticles 114 and/or the non-analytic solution 116 within the groove 606.

To expose the nanostructures 112 and/or nanoparticles 114 for testing and/or detection, the testing strip 602 is removed from the groove 606. The testing device 600 of the illustrated example includes an absorbent 704 that is separated from the non-analytic solution 116 by a portion 706 of the testing strip 602 or associated seal. After the testing strip 602 is removed from the groove 606, the absorbent 704 is exposed to the non-analytic solution 116 and absorbs at least a portion thereof. The environment is then tested for the substance of interest without fear that the test strip 602 had previously been exposed to the substance in a manner to create false positives.

Figure 8:
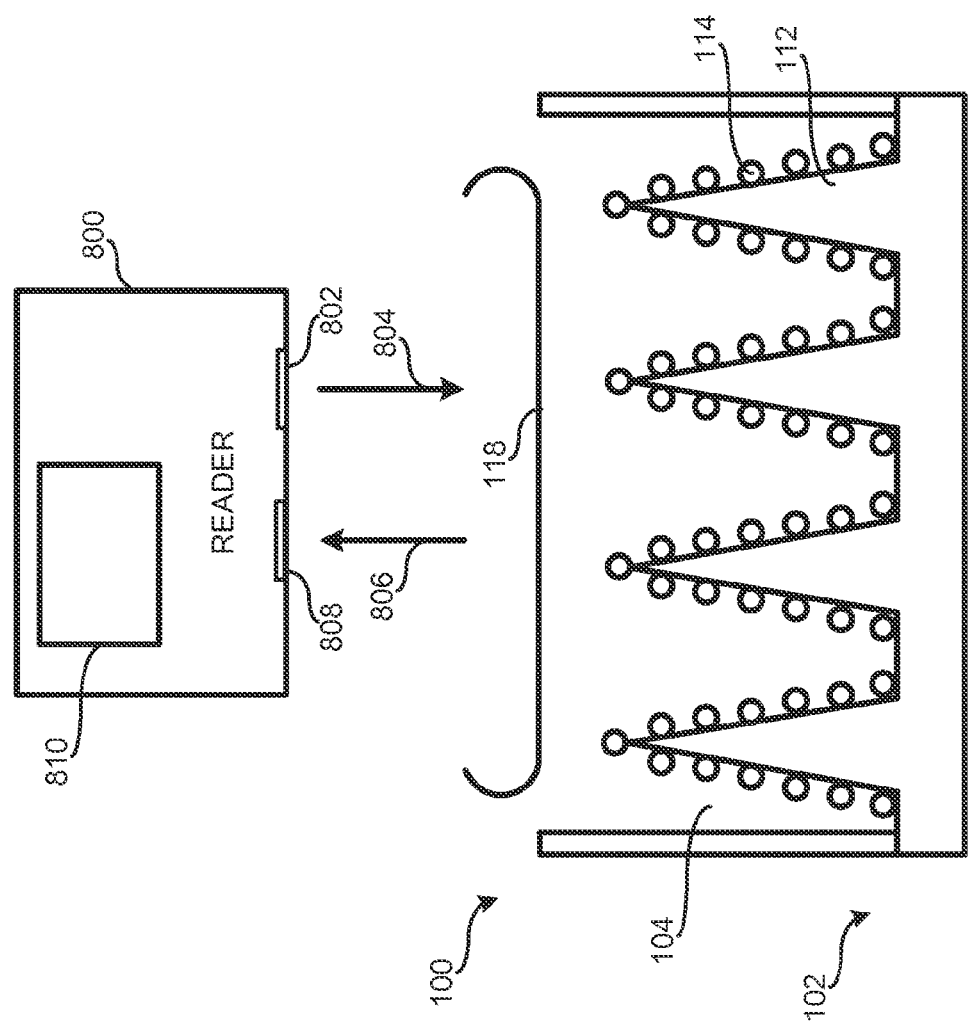
FIG. 8 depicts the example testing device of FIG. 1 and an example reading device constructed in accordance with the teachings of this disclosure.

FIG. 8 illustrates the example testing device 100 of FIG. 1 after exposure to an environment that may contain an analyte(s). FIG. 8 also illustrates an example reading device 800 constructed in accordance with the teachings of this disclosure. In this example, the reading device 800 includes a light source 802 that emits photons 804 through the seal 118 and into the chamber 104 where the photons may be scattered by the nanostructures 112 and/or nanoparticles 114. In some examples, some of the scattered photons 806 are detected and/or monitored by a spectrometer and/or photodetector 808 of the reading device 800. In some examples, the reading device 800 uses the detected and/or monitored photons 806 along with appropriate guiding and/or filtering components to generate results (e.g., information relating to the presence or absence of an analyte to be detected) which are displayed on a monitor 810. Although FIG. 8 shows the testing occurring through the seal 118 in an example in which the seal 118 has been replaced after an environment of interest has been tested, the reading may alternatively be done with the seal 118 removed (e.g., at the test sight, in the environment being tested and/or at a reading site by removing the seal 118).

Figure 9:
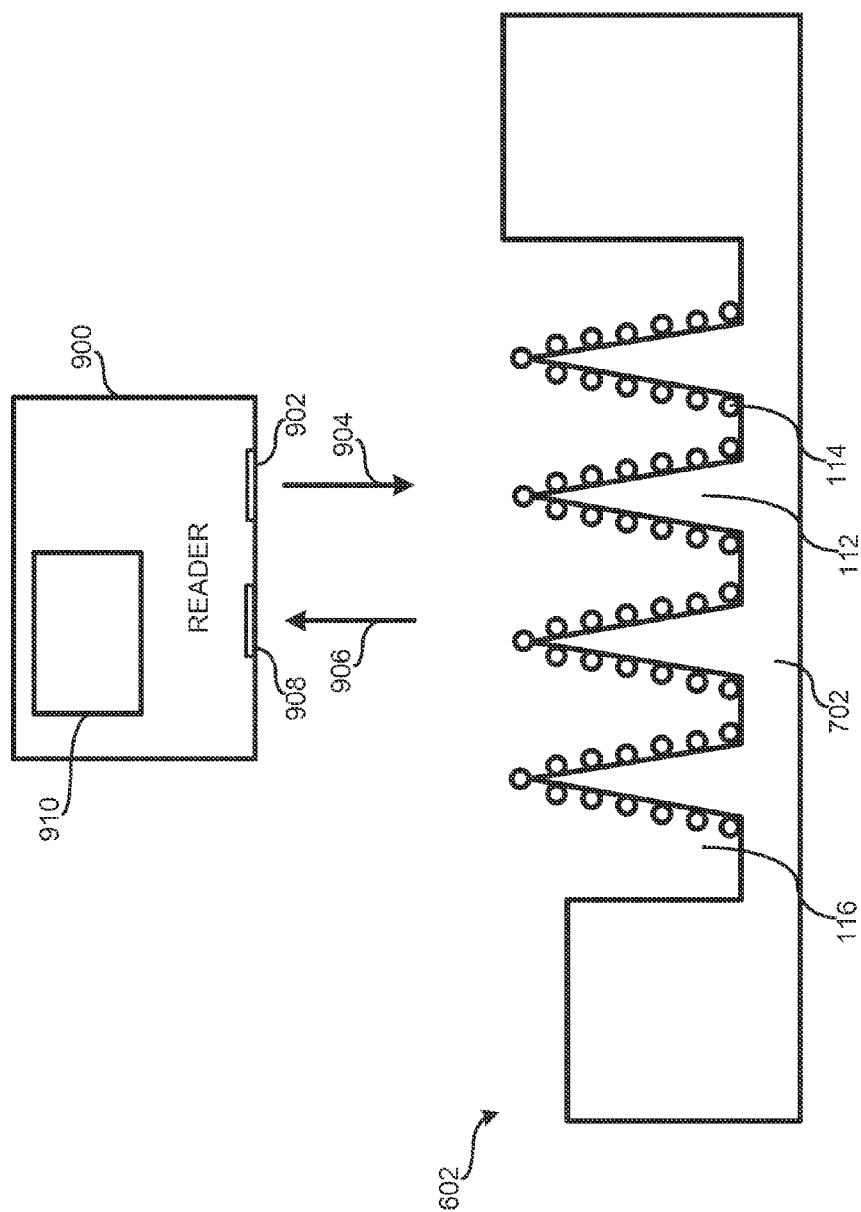
FIG. 9 depicts the example testing device of FIG. 6 and an example reading device constructed in accordance with the teachings of this disclosure.

FIG. 9 illustrates the testing strip 602 after exposure to an environment that may contain an analyte or other substance of interest. FIG. 9 also illustrates an example reading device 900 constructed in accordance with the teachings of this disclosure. The reading device 900 of FIG. 9 may be similar to the reading device 800 of FIG. 8. However, the reading device 800 of FIG. 8 is configured to read the testing device 100 of FIG. 1 and the the reading device 900 of FIG. 9 is configured to read the testing device 600 of FIG. 6. In this example, the reading device 900 includes a light source 902 that emits photons 904 onto the nanostructures 112 and/or nanoparticles 114. In some examples, the nanostructures 112 and/or nanoparticles 114 scatter at least some of the photons 906 which are then detected and/or monitored by a spectrometer and/or photodetector 908 of the reading device 900. In some examples, the reading device 900 uses the detected and/or monitored photons 906 along with appropriate guiding and/or filtering components to generate results (e.g., information relating to the analyte tested) which are displayed on a monitor 910.

Figure 10:
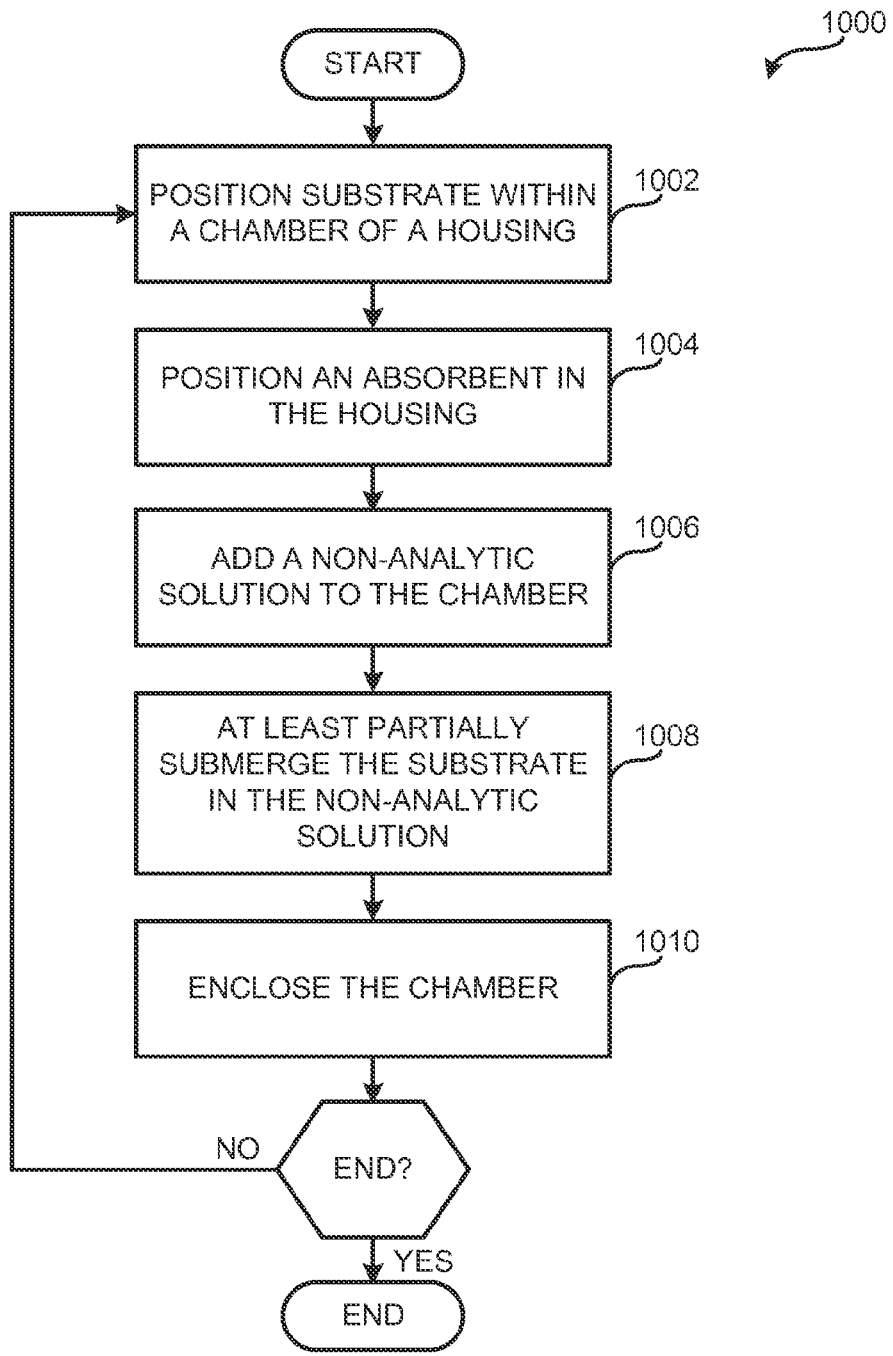
FIG. 10 illustrates an example method of making the examples disclosed herein.

FIG. 10 illustrates an example method 1000 of making the testing devices of FIGS. 1-7 and disclosed herein. Although the example method 1000 of making the testing devices of FIGS. 1-7 are described with reference to the flow diagram of FIG. 10, other methods of implementing the method 1000 of making the testing devices of FIGS. 1-7 may be employed. For example, the order of execution of the blocks may be changed, and/or some of the blocks described may be changed, eliminated, sub-divided, or combined.

The method 1000 may begin by positioning the substrate 106, 702 within a chamber 104, 606 of a housing 102, 604. (block 1002). In some examples, the substrate 106, 702 can evidence exposure to a substance to be tested for when exposed thereto. In some examples, an absorbent 402, 704 is positioned within the housing 102, 604, (block 1004). In some examples, the absorbent 402, 704 is separated from a non-analytic solution to be added to the chamber 104, 106 by a removable seal 404, 706. The non-analytic solution 116 may then be added to the chamber 104, 704 such that the substrate 106, 702 is at least partially submerged by the non-analytic solution 116 within the chamber 104, 704. (blocks 1006 and 1008). The non-analytic solution 116 reduces the possibility that the substrate 106, 702 is prematurely exposed to the substance to be tested for. In some examples, the chamber 104 is then enclosed by the interaction between the seal 118 and the housing 102 and/or the interaction between the testing strip 602 and the housing 604. (block 1010). At block 1010, the method 1000 decides whether or not to return to block 1002. (block 1010).

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A device to detect an analyte substance, comprising:
a housing defining an externally accessible chamber;
a seal to enclose at least a portion of the chamber;
a substrate comprising nanoparticles positioned within the chamber, the nanoparticles to react to the analyte substance when exposed thereto; and
a non-analytic solution, consisting of non-analyte substances, within the chamber to protect the nanoparticles from premature exposure, the chamber being devoid of the analyte substance.

2. The device of claim 1, wherein the non-analytic solution comprises a liquid to reduce premature exposure of the nanoparticles to the analyte.

3. The device of claim 2, wherein the non-analytic solution comprises at least one of water, distilled water, alcohol, ethanol, or a hydrocarbon solution.

4. The device of claim 1, wherein the substrate comprises a Surface Enhanced Raman spectroscopy substrate, a self actuating Surface Enhanced Raman spectroscopy substrate, an Enhanced Fluorescence spectroscopy substrate, or an Enhanced Luminescence spectroscopy substrate.

5. The device of claim 1, wherein the substrate comprises nanostructures, the nanostructures comprising at least one of pillar structures or conical structures.

6. The device of claim 1, wherein the nanostructures are at least partially transparent.

7. The device of claim 1, further comprising an absorbent secured to the housing within the chamber and separated from the non-analytic solution by the seal.

8. The device of claim 7, wherein the absorbent is to at least partially absorb the non-analytic solution after the seal is at least partially removed from the housing.

9. The device of claim 1, wherein the substrate is at least partially submerged in the non-analytic solution.

10. A testing device to detect an analyte, comprising:
a housing defining a groove;
a testing strip sealingly engaging the groove to enclose at least a portion of the groove, the testing strip comprising a substrate positioned within the groove, the substrate to indicate exposure to the analyte if exposed thereto; and
a non-analytic solution, consisting of non-analyte substances, within the groove, the groove being devoid of the analyte.

11. The testing device of claim 10, wherein, if the substance has been exposed to the analyte, the substrate produces spectral components indicating presence of the analyte when the substrate is subjected to a Surface Enhanced Raman spectroscopy, a self actuating Surface Enhanced Raman spectroscopy, an Enhanced Fluorescence spectroscopy, or an Enhanced Luminescence spectroscopy.

12. The testing device of claim 10, wherein the non-analytic solution comprises a liquid to reduce premature exposure of nanoparticles of the substrate to the analyte.

13. The device of claim 1, wherein the substrate forms a floor of the chamber.

14. The testing device of claim 10 further comprising an absorbent supported by the housing within the groove and isolated from the non-analytic solution by the testing strip, wherein the testing strip is separable from the housing to expose the absorbent to the non-analytic solution.

15. The testing device of claim 10, wherein the groove faces in a first direction and wherein the substrate comprises a base and at least one of pillar structures or conical structures projecting from the base in the first direction, the at least one of pillar structures or conical structures extending within the groove between sides of the groove.

16. A device to detect an analyte substance, comprising:
a housing defining an externally accessible chamber;
a seal to enclose at least a portion of the chamber;
a substrate to react to the analyte substance when exposed thereto; and
a non-analytic solution, consisting of non-analyte substances, within the chamber, the chamber being devoid of the analyte substance.

17. The device of claim 16, wherein the substrate comprises at least one of pillar structures or conical structures.

18. The device of claim 17, wherein the seal comprises a membrane extending over said at least one of the pillar structures or conical structures.

19. The device of claim 18, wherein the membrane is releasably glued to the housing over and opposite to the substrate.

20. The device of claim 16 further comprising an absorbent secured to the housing within the chamber, wherein the seal separates the absorbent from the non-analytic solution within the chamber.

* * * * *